US009470776B2

(12) United States Patent
Chan et al.

(10) Patent No.: US 9,470,776 B2
(45) Date of Patent: Oct. 18, 2016

(54) POSITION AND BEHAVIORAL TRACKING SYSTEM AND USES THEREOF (71) Applicant: CASCUBE Ltd., Hong Kong (CN)

(72) Inventors: Chi Shing Chan, Katy, TX (US); Aijun Cao, Sollentuna (SE)

(73) Assignee: CASCUBE LTD, Hong Kong (CN)

( * ) Notice: Subject to any disclaimer, the term of this patent is extended or adjusted under 35 U.S.C. 154(b) by 0 days.

(21) Appl. No.: 14/426,383

(22) PCT Filed: Sep. 5, 2013

(86) PCT No.: PCT/IB2013/058297
§ 371 (c)(1),
(2) Date: Mar. 5, 2015

(87) PCT Pub. No.: WO2014/037890
PCT Pub. Date: Mar. 13, 2014

(65) Prior Publication Data
US 2015/0253414 A1    Sep. 10, 2015

Related U.S. Application Data (60) Provisional application No. 61/697,362, filed on Sep. 6, 2012, provisional application No. 61/780,766, filed on Mar. 13, 2013.

(51) Int. Cl.
*G08B 1/08* (2006.01)
*G01S 5/30* (2006.01)
(Continued)

(52) U.S. Cl.
CPC . *G01S 5/30* (2013.01); *A61B 5/01* (2013.01); *A61B 5/021* (2013.01); *A61B 5/1113* (2013.01); *A61B 2503/40* (2013.01); *A61B 2503/42* (2013.01)

(58) Field of Classification Search
CPC .......................................................... G01S 5/30
USPC ...................................................... 340/539.13
See application file for complete search history.

(56) References Cited

U.S. PATENT DOCUMENTS 5,526,357 A    6/1996 Jandrell
5,915,332 A *  6/1999 Young .................. A01K 29/005
                                                119/421
(Continued)

FOREIGN PATENT DOCUMENTS

CN    101498781    8/2009
CN    102033222    4/2011
(Continued)

OTHER PUBLICATIONS

International Search Report, Feb. 27, 2014, for International Application No. PCT/IB2013/058297.
(Continued)

*Primary Examiner* — Santiago Garcia
(74) *Attorney, Agent, or Firm* — Law Offices of Albert Wai-Kit Chan, PLLC (57) ABSTRACT

This invention provides a system and methods for tracking the positions and behaviors of moving objects such as animals. In one embodiment, the system comprises one or more tracking unit, one or more base nodes, one or more remote data hubs, and one or more remote processor with display. Each tracking unit (e.g. attached or inserted into the tracked animals) could transmit acoustic signal with a unique signature. The base nodes, after time stamping the received signals, relate the signals to the remote processors where the signals will be processed and the 3-dimensional spatial coordinates of the tracking units, and hence the animals, can be identified. Further processing of the positional information would reflect the activities and behaviors of each animal. Additional sensors included in the tracking unit provide further information about the states of the animals such as temperature, heart rate or blood pressure etc.

16 Claims, 7 Drawing Sheets

(51) Int. Cl.
*A61B 5/01* (2006.01)
*A61B 5/021* (2006.01)
*A61B 5/11* (2006.01)

(56) References Cited

U.S. PATENT DOCUMENTS

| | | |
|---|---|---|
| 6,493,649 B1 | 12/2002 | Jones et al. |
| 7,283,423 B2 | 10/2007 | Holm et al. |
| 7,352,652 B2 | 4/2008 | Holm et al. |
| 7,380,435 B1* | 6/2008 | Henderson ............ A01K 1/031 119/712 |
| 7,705,736 B1* | 4/2010 | Kedziora ............ A01K 11/008 340/573.3 |
| 7,928,841 B2 | 4/2011 | Radin |
| 8,031,120 B2 | 10/2011 | Smith et al. |
| 8,149,107 B2 | 4/2012 | Richards et al. |
| 8,154,411 B2 | 4/2012 | Richards et al. |
| 8,955,462 B1* | 2/2015 | Golden ............ A01K 11/008 119/721 |
| 9,226,481 B1* | 1/2016 | Paripati ............ A01K 29/005 |
| 2002/0010390 A1* | 1/2002 | Guice ............ A01K 11/008 600/300 |
| 2004/0141635 A1* | 7/2004 | Liang ............ A61B 5/1113 382/110 |
| 2006/0267167 A1* | 11/2006 | McCain ............ G06K 19/0702 257/678 |
| 2009/0058730 A1* | 3/2009 | Geissler ............ A01K 11/004 342/450 |
| 2010/0090901 A1 | 4/2010 | Smith et al. |
| 2010/0234044 A1 | 9/2010 | Lohbihler |
| 2011/0207402 A1 | 8/2011 | Perkins et al. |
| 2011/0298619 A1* | 12/2011 | O'Hare ............ A01K 11/008 340/573.1 |
| 2012/0015665 A1 | 1/2012 | Farley et al. |
| 2012/0116252 A1 | 5/2012 | Newman et al. |
| 2013/0141237 A1* | 6/2013 | Goetzl ............ A01K 15/021 340/539.13 |
| 2013/0225117 A1* | 8/2013 | Giacoletto ............ H04W 4/22 455/404.2 |
| 2013/0316753 A1* | 11/2013 | Van Dijk ............ A01K 11/006 455/517 |
| 2014/0352632 A1* | 12/2014 | McLaughlin ........ A01K 11/008 119/721 |

FOREIGN PATENT DOCUMENTS

| | | |
|---|---|---|
| CN | 102068261 | 5/2011 |
| CN | 202204926 | 4/2012 |
| CN | 101427543 | 7/2012 |
| GB | 2460032 | 11/2009 |
| WO | 2009094396 | 7/2009 |

OTHER PUBLICATIONS

Written Opinion, Feb. 27, 2014, for International Application No. PCT/IB2013/058297.

Omar, A.M.A. and Omar, A.S., 2005, "Spread Spectrum Ultrasonic Positioning System", In Proceedings of the 2nd Workshop on Positioning, Navigation and Communication (WPNC'05) and 1st Ultra-Wideband Expert Talk (UET'05), Magdeburg, Germany, Mar. 17, 2005, p. 109-114.

Hazas, M. and Hopper, A., 2006, "Broadband Ultrasonic Location Systems for Improved Indoor Positioning", IEEE Transactions on Mobile Computing, 5 (5), p. 536-547.

* cited by examiner

POSITION AND BEHAVIORAL TRACKING SYSTEM AND USES THEREOF

CROSS-REFERENCE TO RELATED APPLICATIONS

This application is the National Stage of International Application No. PCT/IB2013/058297, filed Sep. 5, 2013, which claims benefit of U.S. Ser. No. 61/780,766, filed Mar. 13, 2013 and U.S. Ser. No. 61/697,362, filed Sep. 6, 2012. The contents of the preceding applications are hereby incorporated in their entireties by reference into this application. Throughout this application, various publications are referenced. Disclosures of these publications in their entireties are hereby incorporated by reference into this application in order to more fully describe the state of the art to which this invention pertains.

FIELD OF THE INVENTION

The present invention relates to a local positioning system and uses thereof for precise tracking the position and behavioral activities of a large number of moving objects simultaneously and/or individually.

BACKGROUND OF THE INVENTION

The ability to track the precise location and behaviors of experimental animals is highly desirable such as in laboratory animal testing, which is an indispensable part of many areas of biological research and drug discovery. The precision required in the tracking of small animals is often in the centimeter to sub-centimeter scale in order to detect their subtle movements. GPS-based tracking systems, which have been used for larger animals such as dogs and horses, are therefore inadequate to provide the spatial resolution required.

Traditionally, motion tracking of small animals in laboratories is done by beam breaking of infrared light. However, this method suffers from poor spatial resolution, inability to track more than one animal, and in many cases only two-dimensional movement can be detected. Currently tracking of small laboratory animal activities is based primarily on video capture or pressure-sensing technology. Although providing an improved spatial resolution, these methods still suffer many fundamental limitations that greatly restrict their applications. Among those limitations are: (1) inability to track a large number of animals (dozens to hundreds) simultaneously; (2) no long-term tracking is practically feasible without either enormous human labor and time or data storage; (3) animals have to be transported to testing environments where the tracking systems are located, thus subjecting the animals to stress from the transfer and being in novel environments; (4) setting up and executing the tests involves substantial human interaction with the animals, thus adding stress or other unknown factors to the animals; (5) for video tracking, proper tracking is heavily dependent on the lighting conditions of the environment and skin colors of the animals and thus requires frequent contrast adjustments.

In addition to laboratory animals, precise localization and monitoring of movements is much demanded in other subjects. For example, in plant research, extremely high precision is often required to track the minute movement or growth of different parts within a period of time. Video tracking, though being the only assistive method currently used, is of limited applications due to some of the shortcomings listed above.

There are various principles previously published or currently in use for localizing objects utilizing ultrasound as signal carrier.

As described in U.S. Pat. No. 6,317,368, one ultrasound system uses time delays between a transmitter and several receivers to localize the transmitters and utilizes time division multiple access method for sharing the same frequency channel. The drawbacks of using such channel access method are (i) only one transmitter can be tracked at one time slot, which is not suitable for tracking a large number of objects, (ii) the whole system requires strict synchronization, and (iii) interference may be created at a frequency which is directly connected to the time slot length.

Another ultrasound system, such as that described in U.S. Pat. No. 7,283,423, uses time of arrival from a transmitter to one of the many receivers to localize the transmitters and utilizes the method of frequency division multiple access for channel access. The drawbacks of using such channel access method are that the number of objects being tracked at one given time is limited by the partitions of the frequency band and crosstalk may cause interference among frequencies.

More importantly, the spatial resolution provided by the aforementioned systems is limited by the nature of applied techniques, therefore they are not applicable for more precise localization (millimeter range), such as in tracking the movements of laboratory mice or measuring the daily growth rate of plants etc.

Another shortcoming of the aforementioned systems is that the connection between the ultrasonic receivers and the control center is wired for signal transmission. Such system design requires elaborate hardware and infrastructure setup and is often times not feasible to be carried out in well-established and tightly controlled environments such as animal breeding rooms or laboratories for animal testing.

The present invention uses wireless communication technology as positioning and behavioral tracking system and is designed to overcome the aforementioned limitations.

SUMMARY OF THE INVENTION

In one embodiment, the present invention provides a system for tracking the positions and behaviors of moving objects such as animals. Examples of animals that can be tracked by the present system include, but are not limited to, laboratory mice, rats, hamsters, grey mouse lemur, cats, dogs, macaques, and other non-human primates. In one embodiment, the system comprises one or more tracking units, one or more base nodes, one or more remote data hubs, and one or more remote processors with display.

In one embodiment, the tracking unit is contained within a capsule-like enclosure and includes an acoustic transceiver. In another embodiment, the tracking unit may also comprise components for monitoring bodily functions, for example, the tracking unit may include sensors to measure body temperature, heart rate and blood pressure etc. In one embodiment, the tracking unit can emit acoustic ultrasonic signals that are outside the hearing range of the animals, e.g. at 10 MHz range.

In one embodiment, each base node comprises an acoustic receiver, an electromagnetic (EM) transceiver, a base band for signal processing and synchronization as well as sensors with automatic calibration for various environmental factors such as temperature, humidity and air pressure etc.

Representative examples of remote processor with display include, but are not limited to, workstations, laptop computers, and mobile electronic devices such as mobile phones, tablets and personal digital assistant (PDA) etc. The processors are capable of extracting and processing data from the collected signals to generate three-dimensional positional information of the tracking units, hence the animals, at any time and in real time.

In another embodiment, the present invention also provides methods of using the system disclosed herein to simultaneously track and monitor the movement and behavior of a single to a large number of animals, for example, up to 20 animals, or up to 50, 100, 500, 1000, 5000, or up to 10,000 subjects.

In one embodiment, the method comprises attaching or injecting one or more tracking units to one or more animals, transmitting acoustic signals from the tracking units to one or more base nodes at various rates of data sampling or signal transmission, and sending signals from the base nodes to the remote processor, wherein the collected signals are processed to generate three-dimensional positional information of the tracking units, hence the animals, at any time and in real time.

In one embodiment, the tracking units are attached to the animals via a collar worn by the animals. In another embodiment, the tracking unit are injected into the animals, e.g. by subcutaneous injection. The acoustic signals emitted from each tracking unit carry a unique and specific "signature sequence" as identifier for each animal. The system uses spread-spectrum techniques to allow multiple tracking units to be multiplexed over the same frequency channel at the same time and to minimize potential interference among the transmitted signals.

In one embodiment, the base nodes are located on the walls, on the cages, or other fixtures surrounding the animals. Signal processing includes adding a timestamp to each received incoming signal by the base nodes, sending the time-stamped signals in the form of electromagnetic waves to the remote processors via a remote data hub.

In one embodiment, the remote data hub is a physical module that comprises an EM transceiver and a computer attachment interface, e.g. an USB connector. In another embodiment, the remote data hub is a functional module that is integrated with the remote processor such that a computer attachment interface is not necessary. Upon receiving the signals, the remote processors determine the precise location of each tracking unit by measuring their time of arrival (TOA), or time difference of arrival (TDOA) at the base nodes and generate three-dimensional positional information of the tracking units, hence the animals, in real time. In one embodiment, the positional information is further processed to generate activities and behavioral output for each individual animal. Examples of behavioral output include, but are not limited to, walking/running speed, rearing frequency, percentage time of activity vs. inactivity, turning direction and frequency, copulation duration and frequency, social interactions, aggressive behaviors and maternal behaviors.

The system disclosed herein is capable of tracking movement in the centimeter to sub-centimeter spatial resolution, e.g. in the range of 10 cm to 5 cm, or 5 cm to 1 cm, or 1 cm to 0.5 cm, or 0.5 cm to 0.1 cm etc., in a controlled local area, for example, a breeding room in an animal facility or a laboratory for animal testing. Spatial resolution is achieved via the combination of acoustics and spread spectrum. Spread spectrum techniques not only allow a large number of objects to be tracked simultaneously, individual arrival path can also be identified with a resolution of higher than chip rate. Given that the current radio wave-based GPS system can resolve a difference in location by as small as 1 m, the aforementioned spatial resolution for the present system could easily be achieved when acoustic wave/acoustic transceiver is used instead of radio wave/radio transceiver while everything else remains the same, with the achievable resolution up to almost 1/1 milionth of 1 m since the velocity of radio waves is almost 1 million times higher than that of acoustic waves.

DETAILED DESCRIPTION OF THE INVENTION

Figure 1:
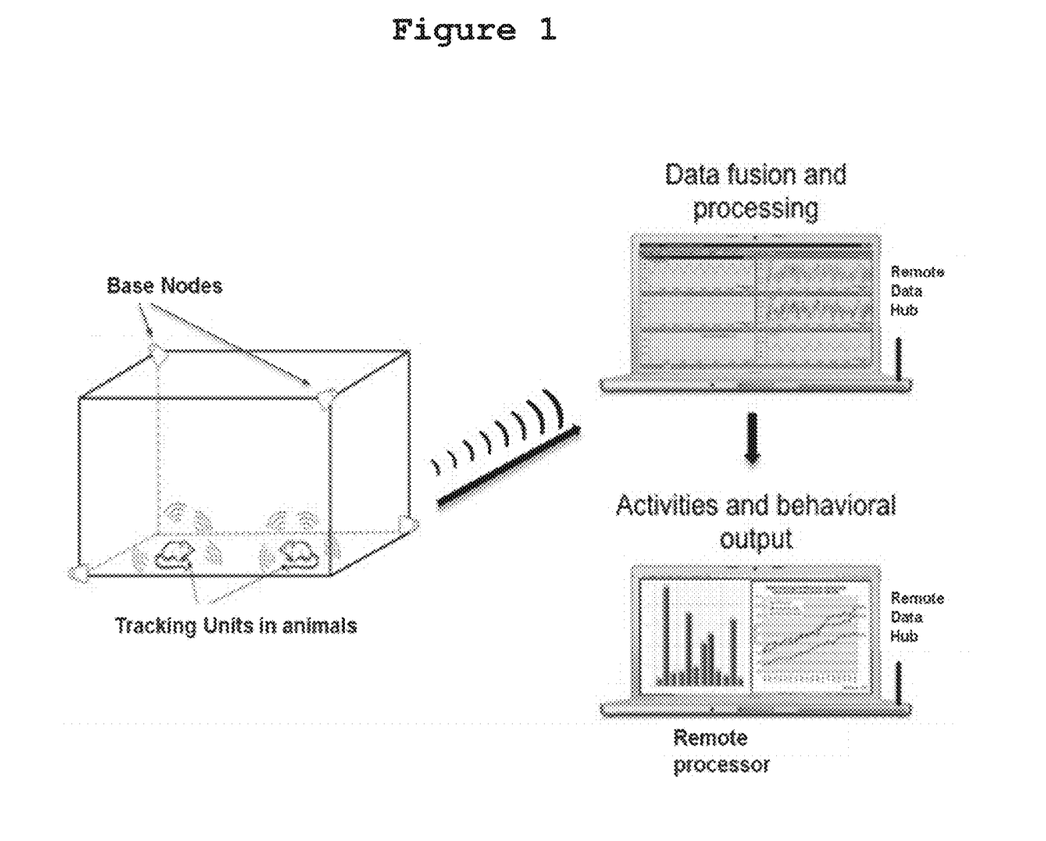
FIG. 1 shows one embodiment of the tracking system as described herein.

In one embodiment, the present invention provides a tracking system comprising one or more tracking units, one or more base nodes, one or more remote data hubs and one or more remote processors with display (e.g. workstations, laptop computers, and mobile electronic devices such as mobile phones, tablets and PDA etc.) (FIG. 1).

Tracking Units

Figure 2:
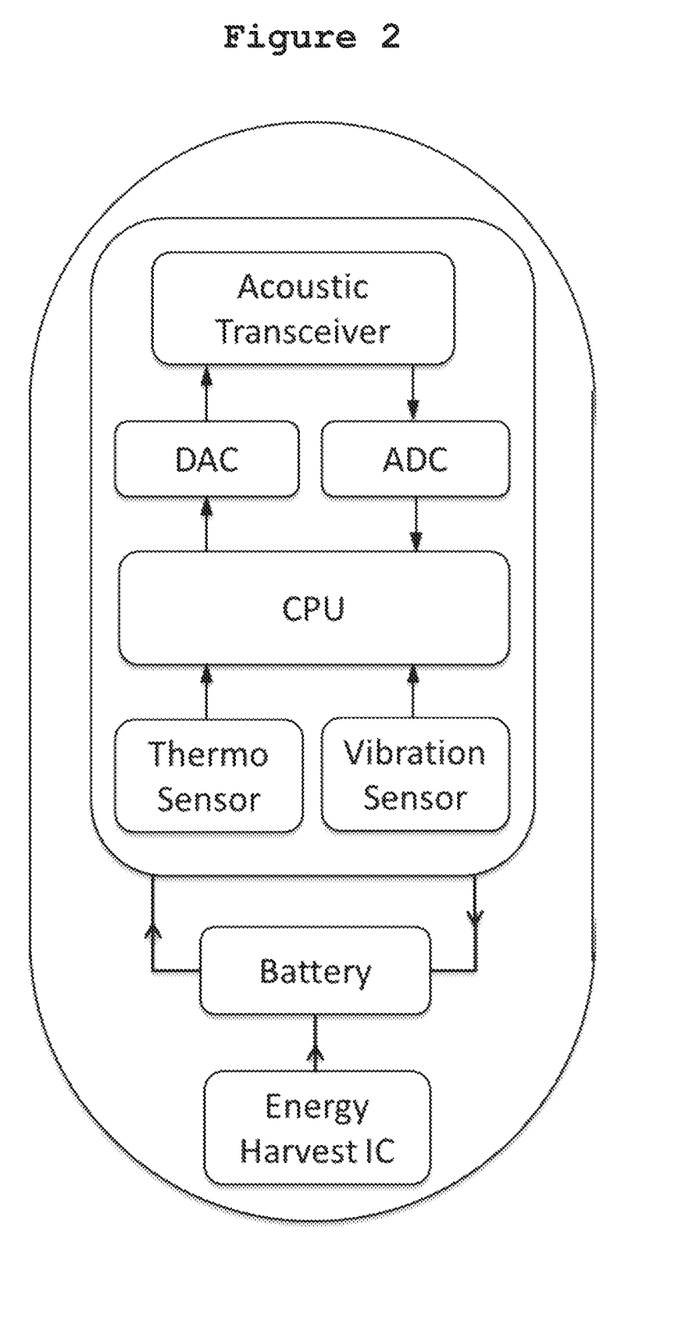
FIG. 2 shows one embodiment of the tracking unit as described herein.

In one embodiment, the tracking unit of the system comprises an acoustic transceiver, a central processing unit (CPU), a battery, an analog-to-digital converter (ADC) and a digital-to-analog converter (DAC), and optional sensors. The acoustic transceiver transmits and receives ultrasonic waves to and from the base nodes. In one embodiment, the acoustic transceivers are ultrasonic acoustic transceivers. In another embodiment, the acoustic transceivers are piezoelectric transceivers or magnetorestrictive transceivers. In yet another embodiment, the acoustic transceivers comprise one or more film transducers. The CPU controls all the transmission parameters (frequency, intensity, duration etc.) and the timing of the transceiver according to the requirements for a particular application. The battery supplies power to all the components of the tracking unit. In one embodiment, the battery can be supplemented with an energy harvesting IC for extended power supply. Depending on the requirements of an application, the optional sensors collect additional physical and physiological information about the animals. This information will then be processed by the CPU and embedded in the transmitted ultrasonic waves. FIG. 2 shows one embodiment of the tracking unit in which a thermo sensor, a vibration sensor, and an energy harvesting IC-coupled battery are included. In one embodiment, the battery in the tracking unit is charged by wireless inductive charging. In another embodiment, the battery is replaceable. In yet another embodiment, the tracking unit is powered with an external power source. In one embodiment, the battery in the tracking unit is lithium or zinc polymer-based ultrathin and flexible type such that it can cover the inner surface and provide sufficient power within the small tracking unit.

The tracking unit emits acoustic ultrasonic signals at MHz range, which is far beyond the animal's upper hearing limit and therefore would not affect the animal's behavior. Since acoustic waves travel at a much slower speed than electromagnetic waves (~874,000 times slower), as acoustic waves travel within the relatively small volume of space monitored by the present invention, the time difference for the signal from a particular tracking unit to reach each of the base nodes at two or more distinct spatial locations would be sufficiently large to pinpoint or detect a change in the spatial position of the source (i.e. the tracking units). For example, in a typical indoor environment the time difference for an acoustic signal emitted from a particular tracking unit to reach each of the base nodes is in the millisecond to microsecond range, which is far below the minimum accuracy level of a common reference clock (e.g. 0.01 ppm at 10 MHz, in nanosecond range) used in the base nodes and the remote processor. In this way, the spatial resolution of the system can achieve millimeter scale. This principal forms one of the key technologies of the invention.

To distinguish all the individual signals, hence the animals, each signal emitted from the transceiver of the tracking unit is embedded in its carrying wave, e.g. by the on/off state or the phase patterns of the waveform, a unique and subject-specific signature sequence (e.g. Walsh Hadamard codes) as identifier that is orthogonal to all other animals' signatures. In one embodiment, the length of the sequence is dependent on the number of subjects to be tracked. In another embodiment, each signature sequence is orthogonal to any other signature sequence, e.g., the inner product of any pair of signature sequences is zero. In this way the base nodes can distinguish each and every animal in a small or large group. In addition, the orthogonal signatures also serve as the key to filter out interference of one signal from all the others. The design of the signature sequence forms one of the key technologies of the invention.

Figure 3:
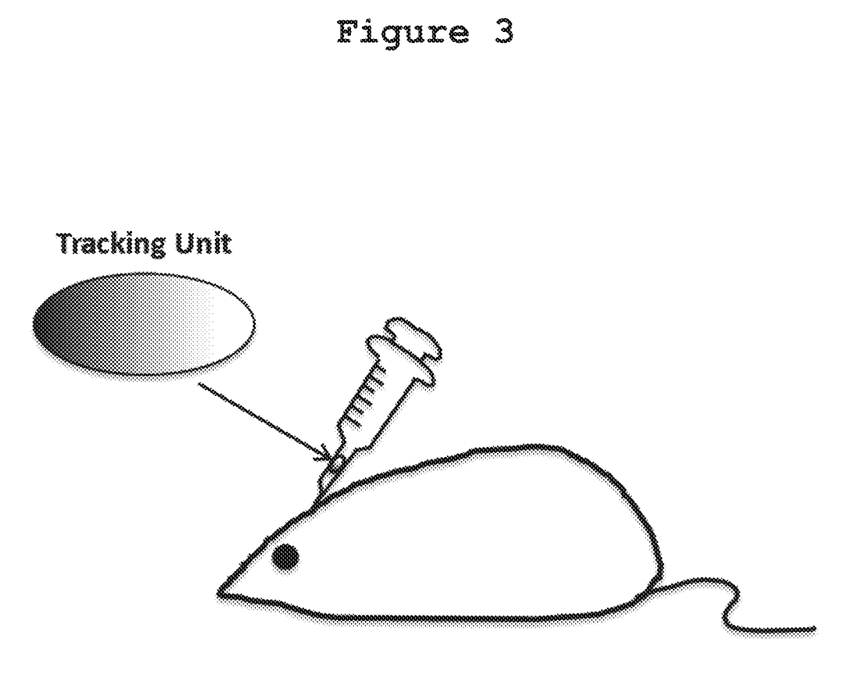
FIG. 3 shows one embodiment of introducing the miniature tracking unit into the animal by subcutaneous injection into the neck area.

For small animals such as laboratory mice, rats, hamsters, grey mouse lemur or other small non-human primates, one of ordinary skill in the art would readily introduce a miniature tracking unit with no more than 10% of the animal's body weight into the animal, for example, by surgery or subcutaneous injection into the animal's neck area using a syringe as shown in FIG. 3. The size of the tracking unit can vary in accordance to the size of the animals. One of ordinary skill in the art would readily construct a capsule-like enclosure for the tracking unit. To aid in keeping the enclosure easily injectable and being non-obstructive to the animal's normal behaviors, e.g. at 1 cm (length) and 0.3 cm (diameter) for laboratory mice, application-specific integrated circuit (ASIC) can be used to further miniaturize the tracking unit when necessary. The material used for the enclosure will be chosen such that it does not interfere with signal transmission and is biologically inert, e.g. polypropylene. Subcutaneous placement of the tracking unit has the advantages of preventing the tracking unit from being dislodged by the animal. Subcutaneous placement would also allow accurate measurements of the animals' physiological status. In one embodiment, the tracking unit may comprise components for the monitoring of bodily functions; for example, the tracking unit may include sensors to measure body temperature, heart rate and blood pressure etc.

When larger animals such as cats, dogs, macaques or other larger non-human primates are being monitored, the tracking unit can be attached to or worn by the animals externally, e.g. enclosed in a collar, for positional and behavioral tracking.

Base Node

Figure 4:
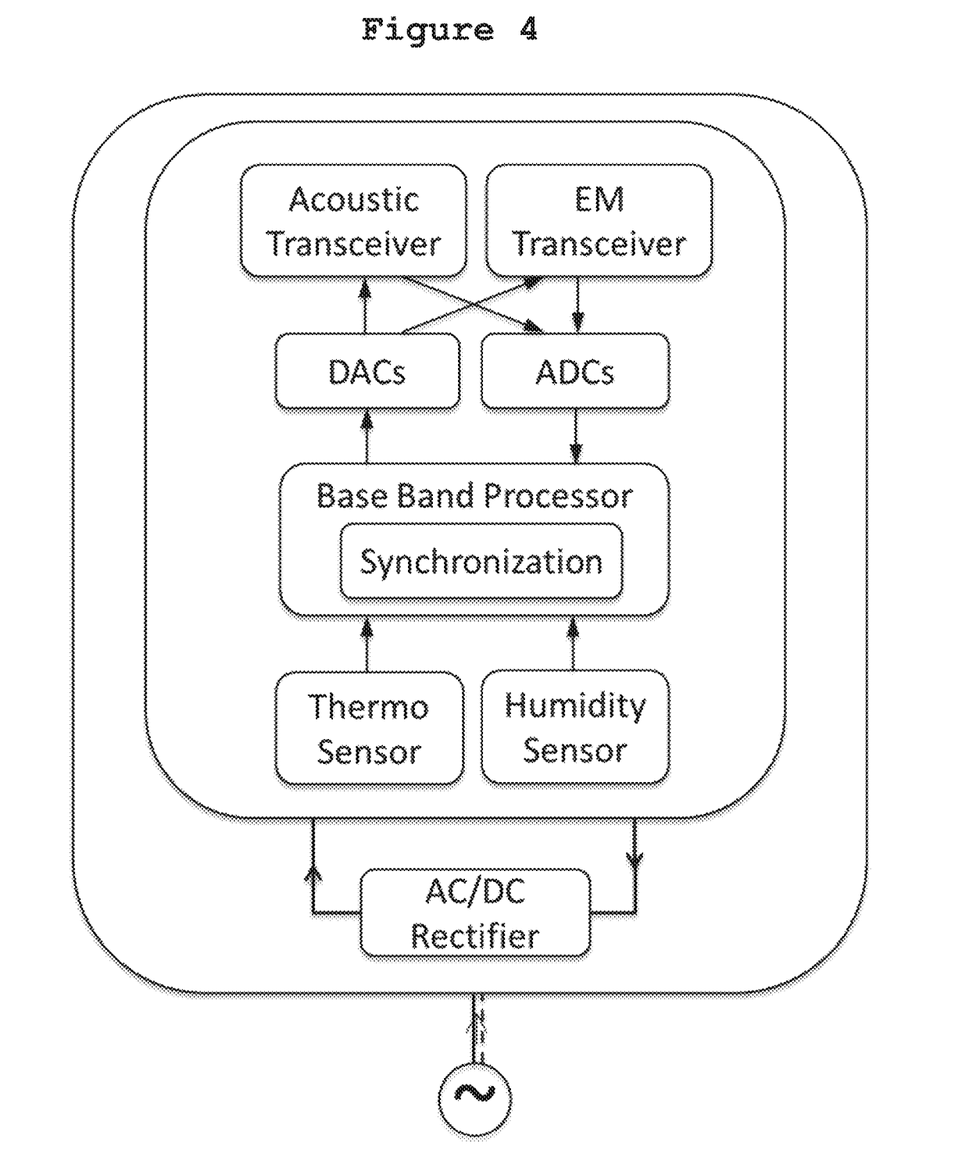
FIG. 4 shows one embodiment of the base node as described herein.

In one embodiment, the base node of the tracking system comprises an acoustic transceiver, an EM transceiver, a base band processor, an AC/DC rectifier, ADCs and DACs, a thermo sensor and a humidity sensor (FIG. 4). In one aspect of the invention, the base nodes are located on the walls or other fixtures surrounding the animals. The number of base nodes can vary depending on the spatial resolution required for the application (more base nodes provide higher resolution) and the capability supported by the remote data hub on the remote processors. Three or more base nodes will be needed for monitoring of events in 3-dimensional space. In one embodiment, the acoustic transceiver is an ultrasonic acoustic transceiver. In another embodiment, the acoustic transceiver is a piezoelectric transducer or a magnetorestrictive transducer. In yet another embodiment, the acoustic transceiver comprises one or more film transducer.

The acoustic transceiver of the base node receives the acoustic signals send from the tracking units and, if necessary, e.g. when relaying instructions from the remote processor, sends acoustic signals back to the tracking units. The EM transceiver sends signals, e.g. radio or infrared, to and, if necessary, receives signals back from the remote processor via the remote data hub. The base band processor carries the timing mechanism of the base node. The AC/DC rectifier converts alternating current entering the base node into direct current and supplies power to all the components of the base node. Since the speed of sound (c) in air is proportional to the square root of temperature (T), $$c=\sqrt{\gamma RT/M}$$

(where $\gamma$ is the adiabatic index of air; R is the universal gas constant; M is the molar mass of air) and both $\gamma$ and M are dependent on humidity, the base node includes thermo and humidity sensors for the precise calculation of the speed of the acoustic waves transmitted from the tracking units.

Since it is crucial that all the clocks in the base nodes and the tracking units are precisely synchronized, an initialization process for clock synchronization must be carried out and their internal clocks are kept synchronized relative to each other. In one embodiment, one of the base nodes is set up as the master, while the rest as slaves. The master node controls how the slave nodes obtain the synchronization by issuing time adjustment commands to the slave nodes. In one embodiment, the master base node is configured such that it periodically transmits a synchronization signature, which is specially designed whose autocorrelation function is close to a sharp delta function, to all the slave base nodes and the tracking units. During the synchronization process the master node starts up, creates the synchronization channel, and enters into the "configuration mode" in which the master base node finds and detects all the slave nodes around it, then transmits the synchronization signals. Upon detecting the arrival of the synchronization signal, the slave base nodes read the synchronization signal and send back an acknowledgement signal to the master. The master base node might then send a timing adjustment command to the slave nodes if needed. This timing adjustment would happen multiple rounds when necessary until all the slave nodes are synchronized to the master node with an accuracy that equals or exceeds the minimum that is required for a given spatial resolution. To prevent the clocks from drifting with time after initialization, this synchronization process is run in each base node periodically to check, correct and maintain the synchronization in all the clocks. In one embodiment, the synchronization process can be performed more frequently in the slave base nodes while synchronization in the tracking units can be performed much less frequently in order to save power.

In one embodiment, the base band processor carries the entire signal processing functions of the base node, which include, but not limited to: analog-to-digital and digital-to-analog conversions, signal synchronization, detection, estimation, equalization, coding and decoding. When a signal from the tracking unit is detected, the base band processor records the position in the time domain corresponding to the precise moment of arrival of that signal. The base band processor then adds this temporal information as a stamp to the subject-specific signature before passing it to the EM transceiver and linking them to the remote processors via the remote data hub in the form of electromagnetic waves using, for example, WiFi, Bluetooth, infra-red or amateur radio frequency band etc.

Remote Data Hub

Figure 5:
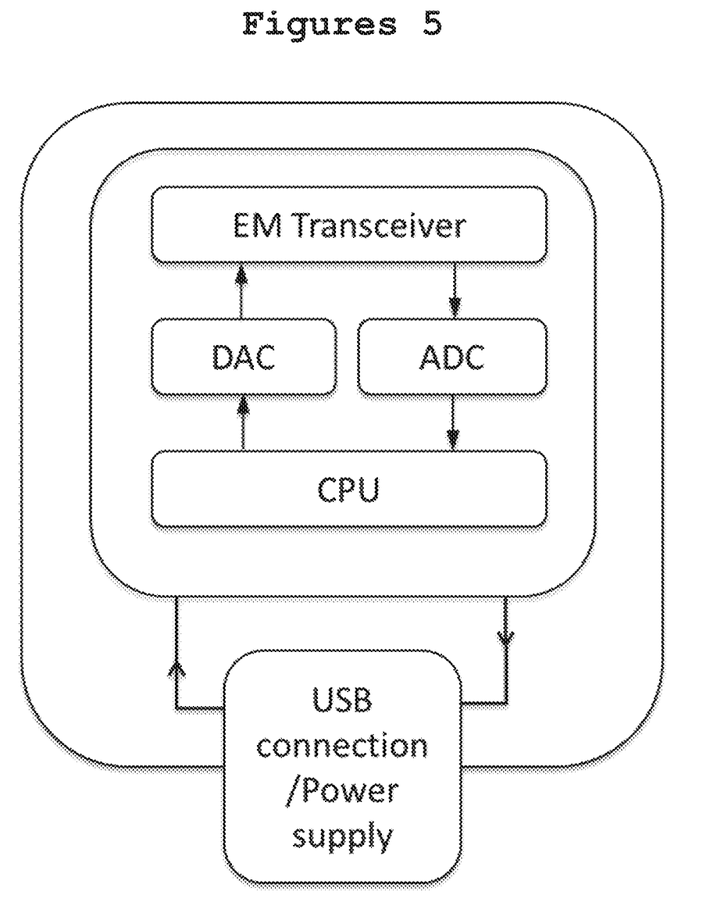
FIG. 5 shows one embodiment of the remote data hub as described herein.

The key function of the remote data hub is to collect all of the signals with time-stamped signatures from the base nodes and relate these signals to the remote processor. In one embodiment, the remote data hub is a physical, standalone module that comprises an EM transceiver, a CPU, an ADC and a DAC, and a power supply. The power supply can be a battery, or in one embodiment, the power can be obtained from the remote processor through a connector such as USB (FIG. 5), FireWire or Thunderbolt connection. In another embodiment, the remote data hub is a functional module that is integrated with the remote processor such that a computer attachment interface is not necessary. The EM transceiver receives electromagnetic signals, e.g. WiFi, Bluetooth, Infrared, or amateur radio signals etc., from the base nodes and, if necessary, sends signals back to the base nodes. It is notable that although signal transfer through wireless connection between the base nodes and the remote data hub is the method of choice due to the ease and flexibility of setting up the system, a wired connection presents an obvious alternative option in circumstances where wireless connection is not feasible or allowed. In one embodiment, the remote data hub is connected to the Internet and transmits data to the remote processor via the Internet. In another embodiment, the remote processor can carry out its function anywhere with internet connection. In yet another embodiment, the remote data hub can store all the data and the remote processor can download the data when there is Internet connection.

Remote Processor

In one embodiment, the remote processor of the tracking system integrates and processes all the signals from every tracking unit into 3-dimensional position information and translates them into behaviors as a function of time. In one embodiment, the remote processors can be any part of a computer or processing unit that perform calculations and/or manipulations of data. For example, the remote processors are the CPU of computing devices such as workstations, laptop computers or hand-held mobile devices (e.g. tablets, PDAs, mobile phones etc.)

Figure 6:
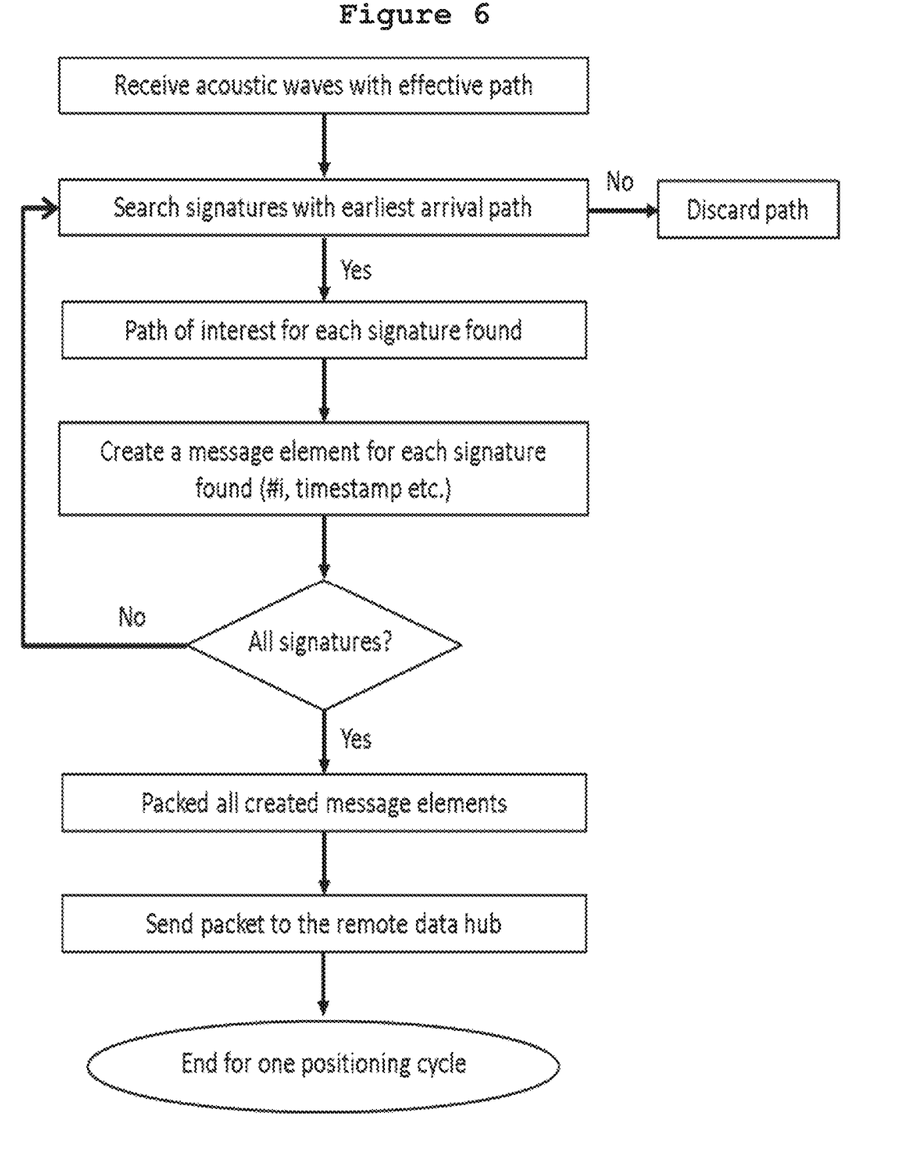
FIG. 6 shows one embodiment of signal processing as described herein.
Figure 7:
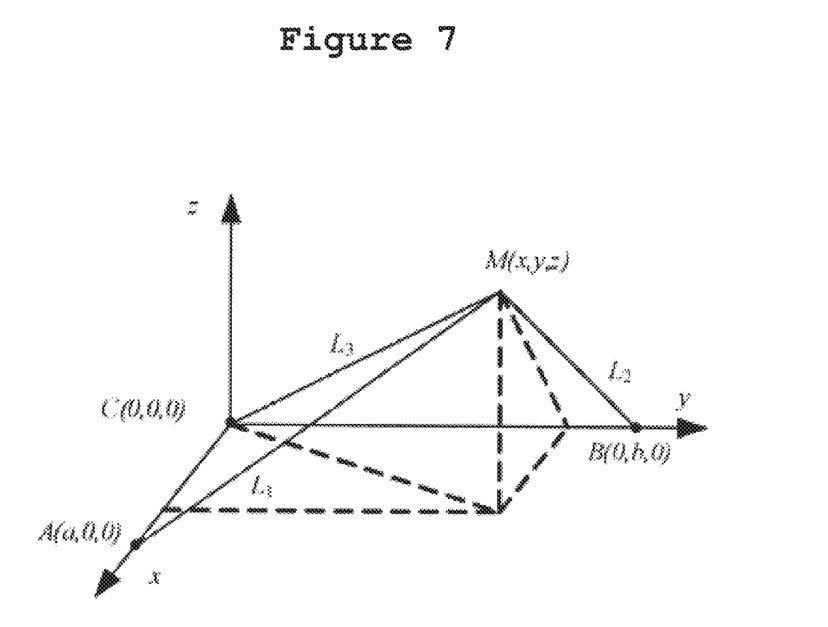
FIG. 7 illustrates the computation of the 3-dimensional positional information by multilateration.

One of the key functions of the remote processor is to determine the arrival of a particular acoustic signal from a tracking unit to a particular base node by performing complex joint signal processing to each detected signal with time-stamped signature. In one embodiment, a relative threshold will first be set based on noise power calculation. Paths above the threshold will be regarded as the effective paths, and the earliest arrival path (line of sight) for each signature is taken as the path of interest (see FIG. 6). In one period (positioning cycle) each tracking unit transmits one positioning burst with a unique positioning signature. Each base node receives the positioning bursts and performs multipath searching. This can be done either for each positioning signature one by one, or for all of the positioning signatures at the same time in parallel, for example, via matrix computation. By comparing the time difference a signal from a particular tracking unit required to reach each of the base nodes, hence the difference in distance between the tracking unit to the different base nodes, the remote processor can compute by multilateration the 3-dimensional positional information of the tracking units, hence the animals, at any time and in real time. As an example, in the case where 3 base nodes are used, the position of a given tracking unit can be obtained as follows:

Suppose A (a,0,0), B (0, b,0) and C (0,0,0) represent the positions of the 3 base nodes, and M (x,y,z) represents the position of the tracking unit in a given space, as illustrated in FIG. 7, the distance between (M and A), (M and B), and (M and C) are L1, L2 and L3, respectively, where $$L1^2 = (a-x)^2 + y^2 + z^2 \qquad (Eq.\ 1.1)$$

$$L2^2 = x^2 + (b-y)^2 + z^2 \qquad (Eq.\ 1.2)$$

$$L3^2 = x^2 + y^2 + z^2 \qquad (Eq.\ 1.3)$$

Solving for x, y and z:

$$x = \frac{L3^2 - L1^2 + a^2}{2a}$$

$$y = \frac{L3^2 - L2^2 + b^2}{2b}$$

$$z = \sqrt{L3^2 - x^2 - y^2} \qquad (Eq.\ 1.6)$$

Since the distance between the tracking unit (M) and a given base node (L) can be calculated, i.e., $$L1 = vt_1 \qquad (Eq.\ 1.7)$$

$$L2 = vt_2 \qquad (Eq.\ 1.8)$$

$$L3 = vt_3 \qquad (Eq.\ 1.9)$$

where v is the speed of sound in air at room temperature, and $t_1$, $t_2$, and $t_3$ are the times the acoustic signal takes to travel from the tracking unit to base node A, B and C, respectively, the value of x,y, and z (i.e. the position of the tracking unit M) can be computed when $t_1$, $t_2$, and $t_3$ are measured (and hence the value L1, L2 and L3) using Eq. 1.4-1.6.

In one embodiment of the invention, the remote processor can send feedback commands, via the remote data hub and base nodes, back to the tracking units to control their properties. For example, a remote processor can send back a new set of parameters to the tracking units to change their rate of data sampling or signal transmission dependent on the time of day. In another embodiment, an additional component, e.g. an electrical pulse generator connected to the muscles of the animals, is integrated as part of and controlled by the CPU of the tracking unit such that a remote processor can instruct this component to alter the activities of the animals, e.g. by stimulating or attenuating muscle contractions.

In one embodiment of the invention, the remote processor can further translate the positional information over a period of time into activities and behavioral output for each individual subject, e.g. walking/running speed, rearing frequency, percentage time of activity vs. inactivity, turning direction and frequency, circling duration and frequency, jumping frequency, hanging duration and frequency, degree of thigmotaxis etc., by determining the change of positions, in three dimensions, as a function of time. For example, by calculating the summation of all the distance traveled in the horizontal axis per unit time over a defined period, the average speed (S) of a subject within this time period can be found, i.e., $$S = \frac{\sum_{t=1}^{n} \sqrt{(x_{t+1} - x_t)^2 + (y_{t+1} - y_t)^2}}{t_n}$$

where x and y are horizontal coordinates of the subject at a given time ($t_n$).

In another embodiment, the rearing-up frequency over a defined period can be counted as the number of times in which the positional change of the subject in the z-axis has exceeded a predefined value, e.g. for mice to be ⅔ of the subject's body length (i.e. approximately the distance between the floor and the neck where the tracking unit is inserted).

In another embodiment, the percentage time of activity (%) over a defined period (T) can be calculated as follows, $$\% = \frac{T_{active}}{T} \times 100$$

where $T_{active}$ is the total time in which there is a change of position of the subject in either x, y, or z axis.

In yet another embodiment of the invention, the remote processor can translate the positional information into interactive activities and behavioral output of multiple animals within a group, e.g. copulation duration and frequency, social interactions, aggressive behaviors and maternal behaviors etc., by analyzing and comparing the relative positions of a selected pair, or multiple, subjects at the corresponding unit time domain, for example, every 1 second. After validating the behavioral output with conventional behavioral tracking methods, e.g. video tracking, the tracking system of the present invention can provide a library of prescribed behaviors for each animal species to allow automatic analysis of the positional information into activities and behavioral output.

In one embodiment of the invention, the information generated by the remote processors can be visualized in real time on the displays associated with the processors. In one embodiment, the output positional and behavioral data can be presented in the forms of texts, tables, charts and graphs etc. The output data can also be exported to other statistics or predictive analytic software, e.g. EXCEL, STATISTICA or SPSS etc., for further customized analysis by the users.

In yet another embodiment of the invention, the remote processor and/or its display, especially when presents in a mobile form, e.g. a laptop or a tablet, should provide a convenient means to pinpoint the identity of any one animal in situ within a group through real-time visualization of the animals' activities. For example, a researcher can select an animal that he wants by using a tablet, located in front of the animal cage for example, that displays real time activities and the identities of all the animals in the cage.

The lifespan of the battery, e.g. lithium-ion or lithium-air, in the tracking unit is designed to last for months so that long-term animal studies can be supported by the tracking system. In one embodiment of the invention, optimization of power consumption of the tracking unit can be achieved by regulating the rate of signal transmission to minimum without significant reduction in the accuracy of tracking and behavioral prediction through validating the behavioral output with conventional tracking systems. In another embodiment, a two-axis motion sensor can be included in the tracking unit such that the tracking unit is set to remain in sleep mode without sending out signals and hence no energy is consumed when no motion is detected from the tracking unit. Mice, for example, roughly spend on average only a quarter of the total time in a day in motion, while they are either sleeping or awake but immobile during the rest of the time. Thus, the battery life of the tracking unit can be extended 3-4 folds by not transmitting signals while the animals are in the immobile state. Notably, an even larger proportion of energy can be saved this way in less active animals than mouse, e.g. rat. In yet another embodiment, the battery life of the tracking unit can be prolonged by linking the battery to an energy harvesting integrated circuits e.g. from kinetic, thermal or piezo sources, such that it can provide sufficient power to the battery throughout the course of the animal study. In one embodiment, the battery in the tracking unit is charged by wireless inductive charging. In another embodiment, the battery is replaceable. In yet another embodiment, the tracking unit is powered with an external power source. In one embodiment, the battery in the tracking unit is lithium or zinc polymer-based ultrathin and flexible type such that it can cover the inner surface and provide sufficient power within the small tracking unit.

In one embodiment of the invention, multiple tracking units can be applied to a single animal to track different parts of the animal simultaneously. For example, four tracking units can be inserted into the four legs of the animal so that the motion of each leg can be individually monitored. Such setup is highly useful in monitoring animals with motor impairment, e.g. animal models for Parkinson's disease, spinal cord injury, stroke etc., where the pattern of motor deficit is important in defining the pathophysiology and the corresponding therapeutic intervention.

In another embodiment of the invention, the tracking system can be used to measure the movements of plants, e.g. elongation, bending or turning of a growing stem tip or other biogenic movements involving various parts of the plant in response to different kinds of stimuli. In one embodiment, lightweight tracking units are placed at the growing tips of the plants so that movements and motion patterns of the growing tips are monitored for an extended period of time. In another embodiment, tracking units are placed on selected leaves such that the movements of the leaves in response to various stimuli, e.g. light, gravity, chemicals, and heat etc., can be monitored. In these embodiments, it is important to ascertain that, by limiting the weight and the size, the tracking units do not affect the native movements of the parts they are monitoring per se.

In another embodiment, an additional component, e.g. a chemical chamber with a release valve connected and controlled by the CPU, is included in the tracking unit such that a remote processor can instruct this component to alter the micro-environment of the plant tissues, e.g. by releasing the chemicals such as ethylene or nitric oxide from the chamber into its vicinity.

In one embodiment, the present invention provides a system for tracking the positions and behaviors of one or more experimental subjects, said system comprises: one or more tracking units, wherein said tracking units are attached or connected to the experimental subjects and are capable of emitting acoustic ultrasonic signals that contain unique signature for each experimental subjects; a plurality of base nodes, wherein said base nodes receive acoustic signals sent from the tracking units, process said signals and send the processed signals to a remote data hub; one or more remote data hubs, wherein said data hubs collect all the signals from the base nodes and relate the signals to one or more remote processors; and one or more remote processors, wherein the processors are capable of processing data from the tracking units to generate three-dimensional positional information for the experimental subjects in real time. Examples of the experimental subjects include, but are not limited to, plants, mice, rats, hamsters, grey mouse lemur, cats, dogs, macaques, or non-human primates.

In one embodiment, the above tracking units are capable of emitting acoustic ultrasonic signals at MHz range. In another embodiment, the tracking units further comprise sensors for monitoring bodily functions of the experimental subjects. Such bodily functions include, but are not limited to, body temperature, heart rate, and blood pressure.

In one embodiment, the above remote data hubs are physical, standalone modules that are physically attached or wirelessly connected to the remote processors. In another embodiment, the remote data hubs are functional modules that are integrated with remote processor. In one embodiment, the remote processors further process the three-dimensional positional information to generate behavioral information for individual experimental subject. Such behavioral information includes, but is not limited to, walking speed, running speed, rearing frequency, percentage time of activity vs. inactivity, and turning direction and frequency. In another embodiment, the remote processors can translate the positional information to reflect interactive activities among multiple experimental subjects.

In one embodiment, the above remote processors further comprise a display so that information generated by the remote processors can be visualized in real time. In another embodiment, the remote processors are further capable of sending feedback commands back to the tracking units to control the operation of the tracking units.

This invention provides a platform for position tracking of subjects within a location defined by the base nodes. The tracking system of the present invention is amendable for various home uses. In one embodiment, the tracking units can be attached to young children and warning signals will be initiated when they become too close to sources of danger, for example, an opened window, or a hot stove. In another embodiment, the tracking units are attached to some or all the valuable objects in a home or a store and warning signals will be initiated when the objects are being moved from their original positions as a means of security measure. In yet another embodiment, small objects in a home could be tracked so that they could be located easily. For example, the tracking units are attached to key chains so that keys could be easily located. In yet another embodiment, the tracking units are attached to the end of long wires, e.g. plugs, USB connectors etc., so that they could be easily located when needed.

The present invention is also adaptable for various medical uses. In one embodiment, the three-dimensional positional information obtained by the present tracking system can be analyzed by the remote processor and warning signals will be initiated when certain criteria is met. For example, the tracking unit can be attached to the neck or body of an elderly person and warning signal will be initiated when the tracking unit is found near or on the floor for a prolonged period of time. In another embodiment, the tracking unit is attached to one or a large number of subjects for tracking movement habits throughout a day. In another embodiment, the tracking units can be attached to areas of interest on subjects, e.g. around joints, to monitor for any abnormalities in movement pattern. In comparison to conventional assessments such as gait analysis, data from all daily activities would be captured rather than the standard patterns such as walking In yet another embodiment, the present invention can be used for tracing the progress of correction of orthopedic deformity, e.g. scoliosis treatment, or improvement in motor function, e.g. physical therapies after spinal cord injury for one or a large number of patients at the same time.

In one embodiment, the present invention can be used in farms for early identification of sick animals. For example, the tracking units of the present invention can be attached to groups of domestic fowl to detect and isolate sick birds before large-scale disease outbreak that can cause huge economic losses.

In another embodiment, the present invention can be used in monitoring of motion of equipment. In one embodiment, the present invention is used in tracking abnormal movement of delicate equipment, such as high-speed centrifuge, during their daily function. In another embodiment, the present invention can be used for predicting the fatigue of mechanical components subjected to daily repeated vibration.

In summary, the present invention provides a system for tracking the positions and behaviors of one or more experimental subjects. Examples of experimental subjects include, but are not limited to, plants, mice, rats, hamsters, grey mouse lemur, cats, dogs, macaques, or non-human primates. In one embodiment, said system comprises: one or more tracking units, wherein said tracking units are attached or connected to the experimental subjects and are capable of emitting acoustic ultrasonic signals that contain unique signature for each experimental subjects; a plurality of base nodes, wherein said base nodes receive acoustic signals sent from the tracking units, process said signals and send the processed signals to a remote data hub; one or more remote data hubs, wherein said data hubs collect all the signals from the base nodes and relate the signals to one or more remote processors; and one or more remote processors, wherein the processors are capable of processing data from the tracking units to generate three-dimensional positional information for the experimental subjects in real time.

In one embodiment, the tracking units of the above system emit acoustic ultrasonic signals at MHz range. In another embodiment, the tracking units further comprise sensors for monitoring bodily functions of the experimental subjects. Such bodily functions include, but are not limited to, body temperature, heart rate, and blood pressure.

In one embodiment, the remote data hubs of the above system are physical modules of the remote processors, e.g. the remote data hubs are physically attached or wirelessly connected to the remote processors. Alternatively, the remote data hubs are functional modules of the remote processors, e.g. the remote data hubs are integrated with the remote processors.

In one embodiment, the remote processors of the above system further process the three-dimensional positional information to generate behavioral information for individual experimental subject. Examples of behavioral information include, but are not limited to, parameters such as walking speed, running speed, rearing frequency, percentage time of activity vs. inactivity, and turning direction and frequency. In another embodiment, the remote processors can translate the positional information to reflect interactive activities among multiple experimental subjects. In another embodiment, the remote processors further comprise a display so that information generated by the remote processors can be visualized in real time. In yet another embodiment, the remote processors are further capable of sending feedback commands back to the tracking units to control the operation of the tracking units.

In another embodiment, the present invention provides a method for tracking the positions and behaviors of one or more experimental subjects in real time, said method comprises the steps of: attaching or injecting one or more tracking units of the system disclosed herein to the experimental subjects; transmitting acoustic signals from the tracking units to the base nodes, and vice versa; sending signals from the base nodes to the remote processor, and vice versa, wherein the remote processor processes the signals to generate three-dimensional positional and behavioral information for the experimental subjects in real time. Examples of the experimental subjects include, but are not limited to, plants, mice, rats, hamsters, grey mouse lemur, cats, dogs, macaques, or non-human primates.

In one embodiment, the above method comprises putting the base nodes on the walls, on the cages, or other fixtures surrounding the experimental subjects. In one embodiment, the above method would generate behavioral information such as walking speed, running speed, rearing frequency, percentage time of activity vs. inactivity, or turning direction and frequency for individual experimental subject. In another embodiment, the above method would generate behavioral information that reflects interactive activities among multiple experimental subjects.

It will be understood that the foregoing description is of preferred exemplary embodiments of the invention, and that the invention is not limited to the specific forms shown. Various modifications may be made in the design and arrangement of the elements described herein without departing from the scope of the invention as described herein.

What is claimed is:

1. A system for tracking the positions and behaviors of one or more experimental subjects, said system comprises:
   one or more tracking units, wherein said tracking units are attached or connected to the experimental subjects and are capable of emitting acoustic ultrasonic signals that contain unique signature for each experimental subjects;
   a plurality of base nodes, wherein said base nodes receive acoustic signals sent from the tracking units, process said signals and send the processed signals to a remote data hub;
   one or more remote data hubs, wherein said data hubs collect all the signals from the base nodes and relate the signals to one or more remote processors, wherein said one or more remote processors are capable of processing data from the tracking units to generate three-dimensional positional information for the experimental subjects in real time with a spatial resolution in centimeter or less; and
   a library comprising data of prescribed behaviors, wherein said three-dimensional positional information is further analysed by said one or more remote processors by comparing to said data in said library to obtain behavioral information for said one or more subjects.

2. The system of claim 1, wherein the tracking units emit acoustic ultrasonic signals at MHz range.

3. The system of claim 1, wherein the tracking units further comprise sensors for monitoring bodily functions of the experimental subjects.

4. The system. of claim 3, wherein the bodily functions are selected. from the group consisting of body temperature, heart rate, and blood pressure.

5. The system of claim 1, wherein the remote data hubs are physical modules or functional modules of the remote processors.

6. The system of claim 1, wherein the three-dimensional positional information has a spatial resolution in millimeter.

7. The system of claim 1, wherein the library comprises one or more parameters selected from the group consisting of walking speed, running speed, rearing frequency, percentage time of activity vs. inactivity, and turning direction and frequency.

8. The system of claim 1, wherein the remote processors can translate the positional information to reflect interactive activities among multiple experimental subjects.

9. The system of claim 1, wherein the remote processors further comprise a display so that information generated by the remote processors can be visualized in real time.

10. The system of claim 1, wherein the remote processors are further capable of sending feedback commands back to the tracking units to control the operation of the tracking units.

11. The system of claim 1, wherein experimental subjects are plants, mice, rats, hamsters, grey mouse lemur, cats, dogs, macaques, or non-human primates.

12. A method for tracking positions and behaviors of one or more experimental subjects in real time, said method comprises the steps of:
   attaching or injecting one or more tracking units of the system of claim 1 to the experimental subjects;
   transmitting acoustic signals from the tracking units to the base nodes, and vice versa, of the system of claim 1; and
   sending signals from the base nodes to the remote processor, and vice versa, of the system of claim 1, wherein the remote processor processes the signals to generate three-dimensional positional and behavioral information for the experimental subjects in real time.

13. The method of claim 12, wherein the experimental subjects are plants, mice, rats, hamsters, grey mouse lemur, cats, dogs, macaques, or non-human primates.

14. The method of claim 12, wherein the base nodes are located on a wall, a cage, or fixtures surrounding the experimental subjects.

15. The method of claim 12, wherein the behavioral information comprises parameters selected. from the group consisting of walking speed, running speed, rearing frequency, percentage time of activity vs. inactivity, and turning direction and frequency.

16. The method of claim 12, wherein the behavioral information reflects interactive activities among multiple experimental subjects.

* * * * *